(12) United States Patent
Glinec et al.

(10) Patent No.: US 10,278,584 B2
(45) Date of Patent: May 7, 2019

(54) METHOD AND SYSTEM FOR THREE-DIMENSIONAL IMAGING

(71) Applicant: Carestream Dental Technology Topco Limited, London (GB)

(72) Inventors: Yannick Glinec, Montevrain (FR); Qinran Chen, Shanghai (CN)

(73) Assignee: Carestream Dental Technology Topco Limited, London (GB)

( * ) Notice: Subject to any disclaimer, the term of this patent is extended or adjusted under 35 U.S.C. 154(b) by 0 days.

(21) Appl. No.: 15/830,593

(22) Filed: Dec. 4, 2017

(65) Prior Publication Data

US 2018/0085002 A1 Mar. 29, 2018

Related U.S. Application Data

(63) Continuation-in-part of application No. 14/767,299, filed as application No. PCT/CN2013/072424 on Mar. 11, 2013, now Pat. No. 9,838,670.

(51) Int. Cl.
*A61B 5/00* (2006.01)
*G06T 7/73* (2017.01)
(Continued)

(52) U.S. Cl.
CPC ........ *A61B 5/0066* (2013.01); *A61B 1/00009* (2013.01); *A61B 1/00055* (2013.01);
(Continued)

(58) Field of Classification Search
CPC .. G06K 9/22; G06K 2209/40; H04N 5/23238; H04N 13/2096; A61C 9/0053;
(Continued)

(56) References Cited

U.S. PATENT DOCUMENTS 9,838,670 B2 * 12/2017 Glinec et al. ........ A61C 9/0053
2002/0006217 A1 1/2002 Rubbert et al. ............... 382/131
(Continued)

FOREIGN PATENT DOCUMENTS

| CN | 101706263 A | 5/2010 |
|---|---|---|
| EP | 2428162 A1 | 3/2012 |

(Continued)

OTHER PUBLICATIONS

Supplementary Partial European Search Report; dated Oct. 27, 2016 for EP Patent Application No. 13877840.2; 2 pages.
(Continued)

*Primary Examiner* — Andrew W Johns

(57) ABSTRACT

A method for three-dimensional imaging stores a first image of field of view from a handheld optical coherence tomography (OCT) scanning device at a first position where a first OCT scan of an object is captured with the scanning device freely operated by a user. A location metric of a second image of field of view of the scanning device is estimated at a second position relative to the first image while the scanning device is moved from the first to the second position. Instructions on providing user feedback are generated based on the location metric. Feedback is provided to indicate if the second position is adequate for a second OCT scan, wherein providing feedback includes providing user perceivable light of a first color to indicate that the second position is adequate and providing user perceivable light of a second color to indicate that the second position is not adequate.

21 Claims, 17 Drawing Sheets

(51) Int. Cl.
    *G06T 7/00*           (2017.01)
    *G06T 7/10*           (2017.01)
    *G06T 11/60*         (2006.01)
    *A61B 1/24*          (2006.01)
    *A61B 1/00*          (2006.01)
    *A61C 9/00*          (2006.01)
    *G06T 19/00*        (2011.01)
    *G06T 11/00*        (2006.01)

(52) U.S. Cl.
    CPC .............. *A61B 1/24* (2013.01); *A61B 5/0088* (2013.01); *A61C 9/0046* (2013.01); *A61C 9/0053* (2013.01); *A61C 9/0073* (2013.01); *G06T 7/0012* (2013.01); *G06T 7/10* (2017.01); *G06T 7/73* (2017.01); *G06T 11/003* (2013.01); *G06T 11/60* (2013.01); *G06T 19/006* (2013.01); *A61B 5/0075* (2013.01); *A61B 2576/00* (2013.01); *G06T 2207/10016* (2013.01); *G06T 2207/10028* (2013.01); *G06T 2207/10101* (2013.01); *G06T 2207/10136* (2013.01); *G06T 2207/20048* (2013.01); *G06T 2207/20221* (2013.01); *G06T 2207/30036* (2013.01); *G06T 2210/41* (2013.01)

(58) Field of Classification Search
    CPC ....... G06T 2200/24; G06T 2207/10028; G06T 2207/20036; G06T 2207/10101; G06T 2207/10132; G06T 2207/10136; A61B 5/0033; A61B 5/0062; A61B 5/0072; A61B 8/12; A61B 8/13
    See application file for complete search history.

(56) References Cited

U.S. PATENT DOCUMENTS

2007/0171220 A1    7/2007   Kriveshko .................... 345/419
2012/0062557 A1    3/2012   Dillon et al. ................. 345/419

FOREIGN PATENT DOCUMENTS

| JP | 11-501174 A | 1/1999 |
| --- | --- | --- |
| JP | 2002-027291 A | 1/2002 |
| JP | 2002-501349 A | 1/2002 |
| JP | 2005-050034 A | 2/2005 |
| JP | 2008-194108 A | 8/2008 |
| JP | 2011-524571 A | 1/2011 |
| JP | 2012-055695 A | 3/2012 |
| JP | 2012-066072 A | 4/2012 |

OTHER PUBLICATIONS

International Search Report, dated Jul. 11, 2013, International Application No. PCT/CN2013/072424; 3 pages.

* cited by examiner

METHOD AND SYSTEM FOR THREE-DIMENSIONAL IMAGING

CROSS REFERENCE TO RELATED APPLICATIONS

This application is a Continuation-in-Part of previously filed application U.S. Ser. No. 14/767,299, entitled "A METHOD AND SYSTEM FOR THREE-DIMENSIONAL IMAGING", filed Aug. 12, 2015 in the names of Y. Glinec and Q. Chen, which itself is a 371 of International Application PCT/CN2013/072424 filed Mar. 11, 2013, all of which are incorporated herein in their entirety.

TECHNICAL FIELD

This invention relates to three-dimensional (3D) imaging of physical object, and more particularly, it relates to a method and system for three-dimensional imaging with a handheld scanning device freely operated by a user.

BACKGROUND

Three-dimensional (3D) imaging technology has been playing an increasingly important role for a wide range of applications, including the production of movies and video games, computer-aided industrial design, orthotics and prosthetics, reverse engineering and prototyping, quality control and inspection, documentation of cultural artifacts, and the like. To facilitate the extensive use of three-dimensional imaging technique by ordinary people, electronic handheld 3D camera product configured with imaging optics have been developed. Due to its portability, such camera devices can be easily handled by the user to analyze a real-world object or environment as needed.

Generally speaking, 3D camera product is designed to collect data on the shape of the object and possibly its appearance, which is then recorded as data points within three-dimensional space. Once a point cloud of geometric samples on the surface of the subject has been obtained, these points can then be used to extrapolate the shape of the subject, for example be converted into a triangulated mesh and then a computer-aided design model. For most situations, it requires multiple scans from many different directions to produce a complete model of the object, usually at least one 3D view being obtained during one scan at a certain perspective. Multiple 3D views are then assembled into a full three-dimensional model, which is often referred to as a "stitching" process.

Various stitching algorithms have been developed, most of which require proper overlap between latest acquired view and previously acquired view to ensure successful and efficient stitching and thus enhance the quality of 3D modeling. For the handheld 3D camera or scanning device products which allow the user to operate freely, i.e. to collect three-dimensional views of the object from substantially random orientations or positions relative to the object, there may exist particular difficulties for the stitching process since a randomly captured view could only mislead the reconstruction, bringing extra burden on calculation rather than a desired result. Prior art does not provide guidance to the user between 3D view captures on how to appropriately locate the scanning device so that the 3D view to be captured may contain useful information for the stitching process. Rather, the operator shall use his or her own judgment on site, and it is often the case that with more scans being conducted, considerable computing time may be required, while the results might often be inaccurate.

BRIEF SUMMARY OF THE INVENTION

It is accordingly an object of the invention to provide a method and system for providing real-time feedback for three-dimensional imaging procedure during the free capture of individual 3D views with handheld scanning devices, which overcomes the above-mentioned disadvantages within the known devices of this general type and which enables more efficient and accurate 3D reconstructions.

With the foregoing and other objects in view, there provides a method for three-dimensional imaging, said method comprising: storing a first two-dimensional image of field of view of a scanning device at a first position where a first three-dimensional view of the object is captured with said handheld scanning device; estimating location metric of a second two-dimensional image of field of view of said scanning device at a second position relative to said first image while said scanning device is being moved from said first position to said second position; and generating instructions on providing feedback to the user based on said location metric; wherein said feedback is provided to indicate if said second position is adequate for capturing a second three-dimensional view.

On another aspect of the present invention, there is also provided a system for three-dimensional imaging, said system comprising: a handheld scanning device freely operated by a user to capture three-dimensional views of an object; a processing unit configured to: store a first two-dimensional image of field of view of said scanning device at a first position where a first three-dimensional view of the object is captured; estimate location metric of a second two-dimensional image of field of view of said scanning device at a second position relative to said first image while said scanning device is being moved from said first position to said second position; generate instructions on providing feedback to the user based on said location metric; and a feedback unit configured to provide said feedback to the user according to said instructions from said processing unit; wherein said feedback is provided to indicate if said second position is adequate for capturing a second three-dimensional view.

The present invention provides directly perceivable feedback on the location of the previously acquired 3D view relative to a new 3D view to be captured, so that the user may be fully aware if the place he or she locates the scanning device for the new 3D view is appropriate for 3D modeling. The feedback is based on the tracking of two-dimensional images in the viewfinder of the scanning device corresponding to the 3D views. Since the feedback is independent of any stitching algorithm in three-dimensional space, the present invention does not introduce noticeable processing cost and time increase. Rather, with the operator of the scanning device knowing where to conduct an effective scan, the 3D stitching process may be substantially enhances, in terms of both speed and quality.

Other features of the invention, its nature and various advantages will be apparent from the accompanying drawings and the following detailed description of certain preferred embodiments.

BRIEF DESCRIPTION OF THE DRAWINGS

The foregoing and other objects, features, and advantages of the invention will be apparent from the following more particular description of preferred embodiments as illustrated in the accompanying drawings, in which.

DETAILED DESCRIPTION

Figure 1:
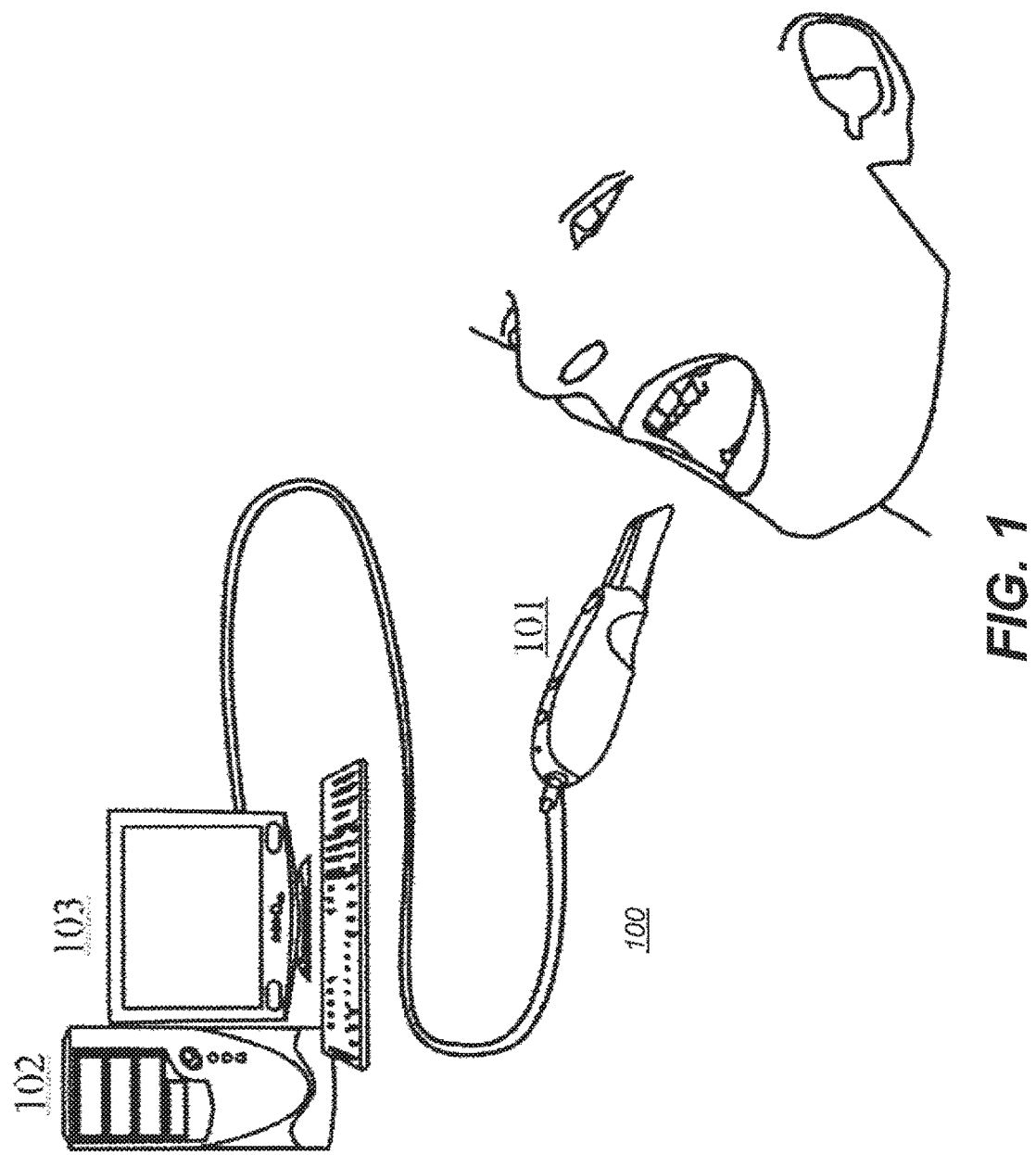
FIG. 1 illustrates a system for three-dimensional imaging according to one embodiment of the invention.

While the invention covers various modifications and alternative constructions, embodiments of the invention are shown in the drawings and will hereinafter be described in detail. However it should be understood that the specific description and drawings are not intended to limit the invention to the specific forms disclosed. On the contrary, it is intended that the scope of the claimed invention includes all modifications and alternative constructions thereof falling within the scope of the invention as expressed in the appended claims.

Unless defined in the context of the present description, otherwise, all technical and scientific terms used herein have the same meaning as commonly understood by one of ordinary skill in the art to which this invention belongs.

It is described below a technique for providing real-time feedback to a user operating a three dimensional scanning device for three-dimensional imaging. However, it will be appreciated that the inventive concepts disclosed herein are not limited to such applications, and may be usefully employed in a variety of imaging applications. For example, the system and method described herein may be usefully employed in two-dimensional imaging systems or other applications where the imaging could be enhanced by a real-time feedback. All such variations and alternative embodiments as would be apparent to one of ordinary skill in the art are intended to fall within the scope of this disclosure.

Moreover, by way of a non-limiting example, the methods and arrangements of the present disclosure may be illustrated by being used in dental imaging. However, it should be understood that the teaching of the present disclosure can be applied to similar 3D imaging procedure, where the generation of the object surface in three dimensions is based on stitching of several 3D views captured at arbitrary orientation relative to the object with a scanning device under free control of a user.

FIG. 1 illustrates a system for three-dimensional imaging according to one embodiment of the invention. System 100 may be applied to prosthodontics procedures designed to implant a dental prosthesis in the intra oral cavity, providing three-dimensional modeling result for a prosthesis such as a crown. According to the embodiment shown in FIG. 1, system 100 may at least comprise a handheld scanning device 101, a processing unit 102 and a feedback unit 103.

As shown in FIG. 1, the handheld scanning device is in the shape of a probe, which could be freely operated, i.e., positioned by a user. However, this kind of handheld scanning device, also termed as hand-piece herein for simplicity, could be configured into any shape, as long as it could provide the user with sufficient convenience in its moving and operating. Basically, the handheld scanning device 101 may be manipulated by the user to capture three-dimensional views of an object from different positions, for example, while there is generally no rules for the sequence of the 3D views to be captured. For example, hand-piece 101 may serve as an intra-oral camera in the illustrated embodiment, where the object could be the jaw, tooth or gum of a patient.

Figure 2:
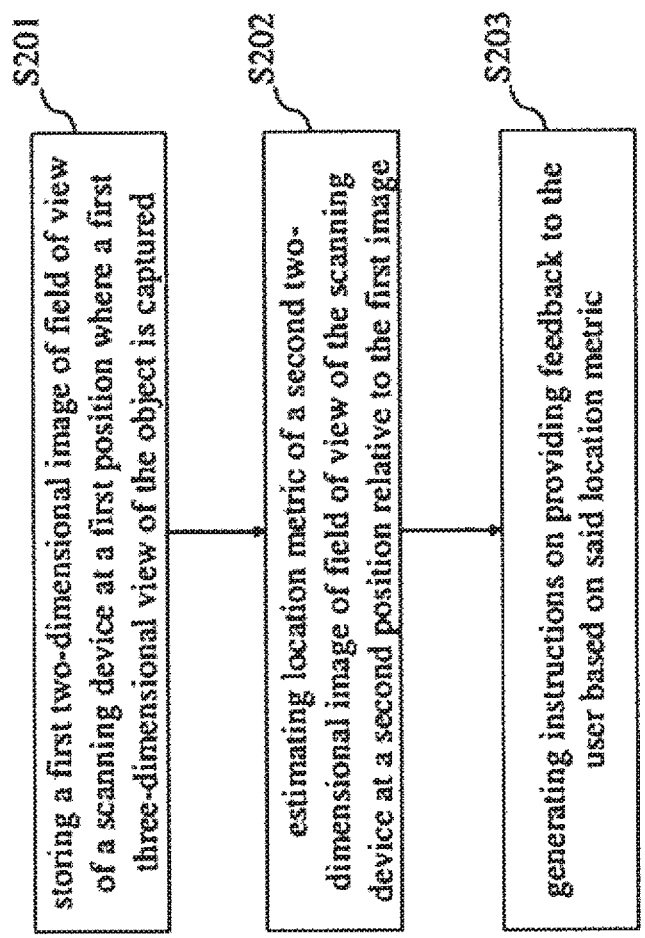
FIG. 2 illustrates a process for three-dimensional imaging according to one embodiment of the invention.

The processing unit 102 may be configured to execute the steps as illustrated in FIG. 2, where a process for three-dimensional imaging according to one embodiment of the present invention is illustrated. Particularly, the processing is configured to store (S201) a first two-dimensional image of field of view of scanning device 101 at a first position where a first three-dimensional view of the object is captured; estimate (S202) location metric of a second two-dimensional image of field of view of scanning device 101 at a second position relative to said first image while the scanning device 101 is being moved from said first position to said second position; and generate (S203) instructions on providing feedback to the user based on the location metric. In embodiments of the present invention, the feedback is provided to indicate if the second position is adequate for capturing a second three-dimensional view for stitching process in three-dimensional imaging procedure.

Processing unit 102 is shown as a personal computer in FIG. 1. It is to be understood that it may implemented in, for example, any suitable processing platform, computing platform, computing device, processing device, computing system, processing system, computer, processor, or the like, and may be implemented using any suitable combination of hardware and/or software, as may be suitable for specific applications or in accordance with specific design requirements.

As mentioned above, in order to obtain a view for the global surface of an object, more than one 3D views shall be successively captured from different perspectives and the three-dimensional data for each view may be "stitched" all together at the same time or stitched to existing three-dimensional model using various stitching algorithms. Either way, an appropriate overlap between the captured 3D views is critical to the success and efficiency of the stitching process and to the quality of the modeling result. While benefiting from the free control of the handheld equipment, users may not be fully aware of where to position the hand-piece so as to enhance the efficiency and accuracy of the 3D modeling procedure. For a 3D imaging system which is configured to provide visual image of field of view of the scanning device, the user often has no clue about the position where last 3D view was captured relative to the video image currently being shown on the screen after the movement of the scanning device.

Processing unit 102 is configured to generate instructions on providing feedback to the user between two 3D view captures, i.e., after one 3D view has been obtained and before another scan is to be conducted. With the help of such real-time feedback, users could be warned or notified if the current placement of the scanning device 101 is adequate for capturing another 3D view, which is advantageous to the stitching process.

As mentioned above, the instructions on providing feedback to the user is generated based on estimated location metric of a 2D image of field of view of scanning device 101 at its current position, i.e., the second image, relative to the stored image of its field of view at the previous position where last 3D view was captured, i.e., the first image. For example, the location metric may be estimated as the overlap between the first image and the second image or the rotation angle between the first image and the second image. In one embodiment of the present invention, if the overlap is estimated to be above 30% or if the rotation angle is estimated to be less than 30 degrees, feedback may be provided to indicate that the second position where a new 3D view is to be captured is acceptable for the stitching process.

For guarantee success of 3D imaging procedure, the goal is to estimate the overlap of a new 3D view with the mesh surface acquired during last scan. User guidance based on 3D reconstruction of the captured data during the movement of scanning device may provide more stable results, but also may suffer from real-time constraints and complexity of algorithm, which would probably bring no benefits. By contrast, in embodiments of the present invention, feedback on the placement of the scanning device is independent from the 3D reconstruction algorithm. The candidate position for a new 3D view is evaluated simply from a measure of relative location between corresponding two-dimensional images, assuming that the overlap between 3D views can be reflected by the overlap between corresponding 2D images. Perspective viewing, where object surfaces might be occluded, and missing parts in the 3D view (due to lack of signal in regions of low reflectivity for instance) are two reasons why this assumption is not valid. However, since the object of the present invention is only to guide the operator and provide reference information, the accuracy of this measure does not need to be extremely precise. The process for estimating location metric will be exemplified below with respect to FIG. 3.

Feedback unit 103 is designed to function according to the instructions from the processing unit 102, i.e., to provide said feedback to the user according to the instruction generated by processing unit 102.

In the embodiment as illustrated in FIG. 1, feedback unit 103 is implemented as a monitor, where live video images of field of view of scanning device 101 may be rendered to assist the operator in positioning the scanning device relative to the object. In one embodiments of the present invention. In this case, the instructions on providing feedback may include displaying representation of the first image superimposed on the live video images. This superposition of a sign of the first image may indicate to a user both where the scanning device 101 is currently positioned and how the scanning device has been moved relative to the position where last scan was conducted. To provide the effect of real-time tracking. The location and appearance of the representation may be configured to change with the moving of said scanning device, so that the user may have a clear vision of how the scanning device 101 has been moved from where last scan was conducted.

Figure 4C:
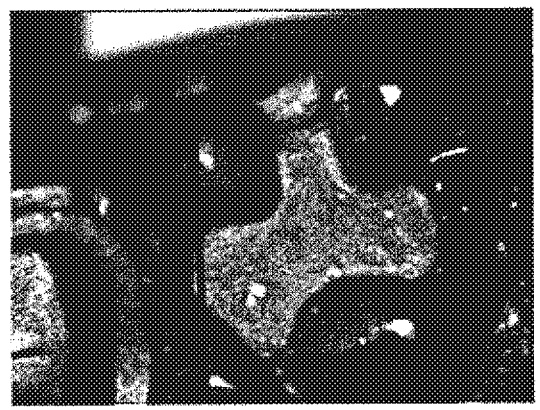
FIGS. 4a, 4b and 4c depict views for providing feedback to the user according to one embodiment of the present invention.
Figure 4B:
Figure 4A:
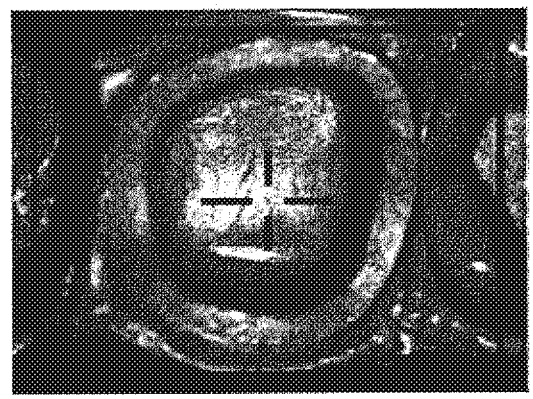

An example could be seen in FIG. 4a, FIG. 4b and FIG. 4c, where the representation of the first image is a rectangle with a cross inside. FIG. 4a shows the field of view of scanning device 101 at the first position when last 3D view was being captured, i.e., the first image, where the rectangle and the cross is located right in the middle of the screen without any distortion. FIG. 4b shows the field of view of scanning device 101 when it is positioned at a second site, where the deformation and displacement of the rectangle and the cross on the screen may reflect the rotation, translation and tilt of the scanning device relative to the position where last scan was conducted. The color code of the frame indicates a suitable position for acquisition of a 3D view. FIG. 4c shows the field of view of a scanning device 101 when positioned at another second site, where the orange color of the frame indicates a non-recommended place for acquisition of a 3D view. In some cases, the representation of the first frame may only be partially displayed, since the scanning device has been moved far away from the initial place.

Preferably, to provide a directly perceivable indication of whether the current position is appropriate to capture another 3D view, the representation of the first frame may be configured to present a first color, for example green to indicate the second position is adequate (FIG. 4b) and a second color, like orange to indicate the second position is not adequate (FIG. 4c).

In another embodiment of the present invention, feedback unit 103 may be implemented as a light emitting component integrated with scanning device 101, for example, attached to one side of the body of the scanning device. For example, the light emitting component may include any light projector and light emitting buttons or diodes. In one embodiment of the present invention, there may be a LED ring around the capture button on the hand-piece that can change the color of light. The light emitting component may emit light of a first color, for example green to indicate the second position is adequate and emit light of a second color, like red to indicate the second position is not adequate. In this case, whether or not any live vision of the captured image is provided, the user may be aware of how to locate the scanning device by looking at the emitted color directly from the hand-piece, without having to watch at the display of the processing unit.

In still another embodiment of the present invention, feedback unit 103 may be implemented as an image projector. Feedback as to the displacement of the scanning device 101 may be provided by projecting images onto the object through the image projector.

Figure 5:
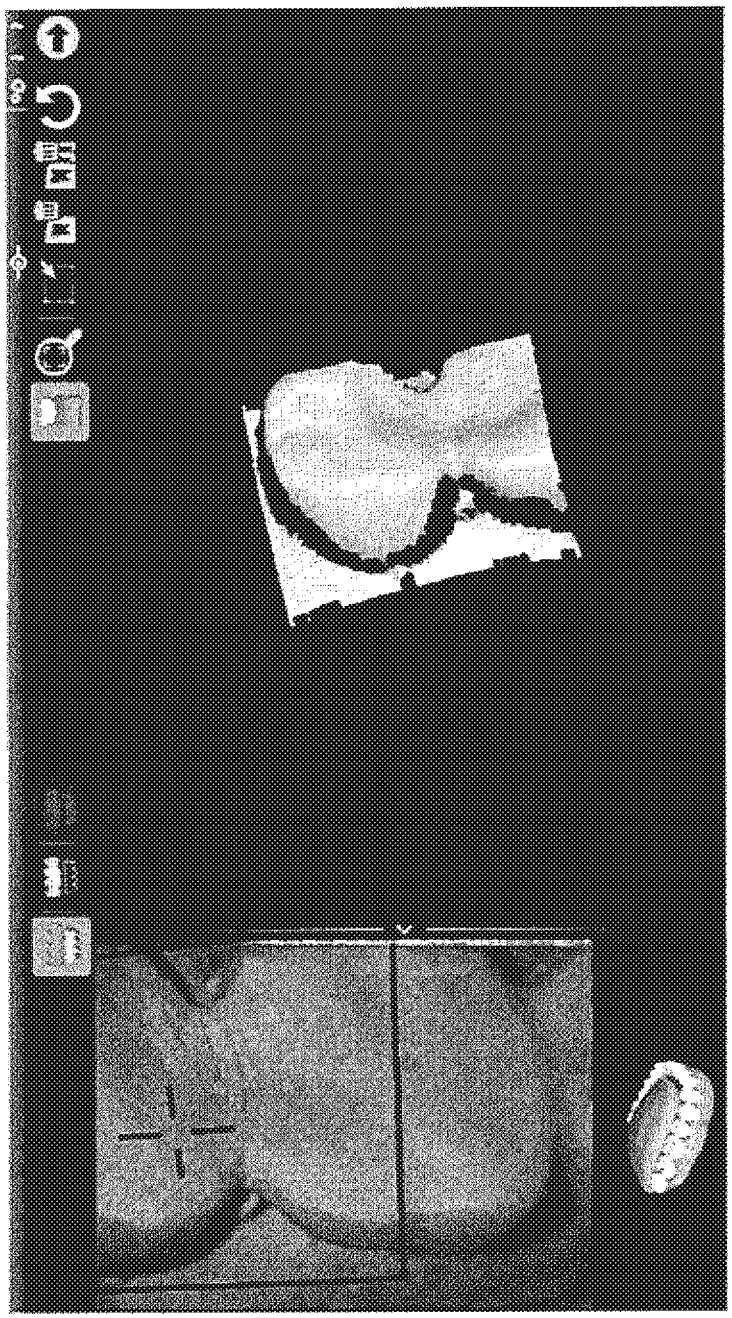
FIG. 5 depicts a view for providing feedback to the user according to another embodiment of the present invention.

FIG. 5 depicts an exemplary view for providing feedback through an image projector in dental application, where the object is the patient's teeth. The projected image could be the distorted rectangle and crosses as shown on the computer screen or could also be a projection of already acquired 3D views. The 3D surface on the right was acquired at the first position. Based on the estimated location metric of the second image relative to the first image, we have enough knowledge to place the 3D surface from the right onto the video frame, inside the rectangle, which may be shown as green. That is, the image projector may be configured to directly project the 3D surface on the right onto the teeth surface, at proper location relative to the current view. The live view is provided on the left for the purpose of illustration, while in practice, the user may see the 3D surface inside the mouth with his eyes, without looking at the screen.

With the help of appropriate feedback between two captures, computation resources could be saved to some degree since misleading or useless information resulted from the arbitrary positioning and orientation of the scanning device has been largely reduced. The stitching process for 3D imaging could be more smoothly and efficiently carried out, and thus enhancing accuracy of the final results.

It is to be understood by those skilled in the art that the structure of system 100 as illustrated in FIG. 1 is only provided for exemplary purpose. Though scanning device 101, processing unit 102 and feedback unit 103 are shown as separate pieces, they could be implemented as an integration. For example, processing unit 102 may be integrated within the hand-piece device, which may further equipped with a screen for providing real-time feedback. In another implementation, feedback unit 103 may also be incorporated into a processing device, like when a laptop is being used to communicate with the scanning device 101. Generally, embodiments of the present invention may include units and/or sub-units, which may be separate of each other or combined together, in whole or in part, and may be implemented using specific, multipurpose or general processors or controllers, or devices as are known in the art.

It is to be noted that stitching in two dimensions is much less complicated than the 3D stitching procedure. The two dimensional stitch could provide a transformation matrix, which contains the information on the spatial transform between corresponding pixel on the two images being stitched. Such transformation matrix is usually created as a square matrix, which provides a linear relationship between a 2D point from one image and a corresponding 2D points on a second image. In the field of this invention, a 2D point (x, y) is represented using homogeneous coordinates (x, y, 1). For homogeneous coordinates, such transformation matrix is defined as a homography matrix. In the field of computer vision, any two images of the same planar surface in space may be related by a homography matrix. A general 3×3 homography matrix H for transforming 2D pixel coordinates from $(x_2,y_2)$ to $(x_1,y_1)$ can be written as:

$$H = \begin{bmatrix} h_{11} & h_{12} & h_{13} \\ h_{21} & h_{22} & h_{23} \\ h_{31} & h_{32} & h_{33} \end{bmatrix}$$

such that:

$$\begin{bmatrix} wx_1 \\ wy_1 \\ w \end{bmatrix} = H \begin{bmatrix} x_2 \\ y_2 \\ 1 \end{bmatrix},$$

where w is a perspective parameter and is determined by that equation.

In the case of affine transform, $h_{31}=h_{32}=0$ and $h_{33}=1$. The remaining 6 degrees of freedom from the affine transform can be rewritten using an equivalent more classic representation as below:

$$H = \begin{bmatrix} s_x\cos\theta & s_x\sin\theta & t_x \\ -s_y\sin\theta + k\cos\theta & s_y\cos\theta + k\sin\theta & t_y \\ 0 & 0 & 1 \end{bmatrix}$$

wherein θ represents rotation angle between the two images, $(s_x, s_y)$ is a measure of scaling in two dimensions along the x and y axes of the second image respectively, w represents the skew between the two images, and $(t_x, t_y)$ is a measure of translation in two dimensions along x and y axes of the second image respectively In one embodiment of the present invention, stitching one image with another image to obtain the transformation matrix may include: 1. detect feature points in each image; 2. limit number of features; 3. extract feature descriptors for each image at feature locations; 4. match image descriptors using an exhaustive search algorithm, such as RANdom SAmple Consensus (RANSAC), which may be performed for the first image against the second image and vice versa; 5. keep symmetric matches only, i.e., when best match for feature f1 in the first image is f2 on the second image and best match for f2 is f1. One iteration of the RANSAC algorithm randomly picks 3 pairs of feature points from the above symmetric matches to compute a candidate transformation matrix, then determines how many other matches agree with the candidate transformation matrix by computing the distance between the transformed first point from the match and the target second point from the match. The match is said to agree with the transform if the distance falls below a predetermined threshold. Subsequent iterations of the RANSAC algorithm are performed, which may stop after a predetermined number of times. The candidate transformation matrix which had the highest number of matches that agree with it is selected as the transformation matrix.

This feature-based matching approach for image stitching is only described as an example. Any other strategies for computing transformation in computer vision may be used in embodiments of the present invention.

The estimation of the location metric between the first and second images can be done either directly between these images, or indirectly through the use of a reference image. At the beginning of the image sequence of field of views from scanning device 101 following the first frame, there should have enough overlap between first and second image for the stitching to be successful. But as the hand-piece moves away, the overlap between these two frames might not be sufficient to obtain accurate location metric. This explains why it is desired to have a reference image, which is selected during the image sequence of field of views, acting as an intermediate to allow location metric of the second image relative to the first image to be determined even when the first and second images don't overlap anymore.

Figure 3:
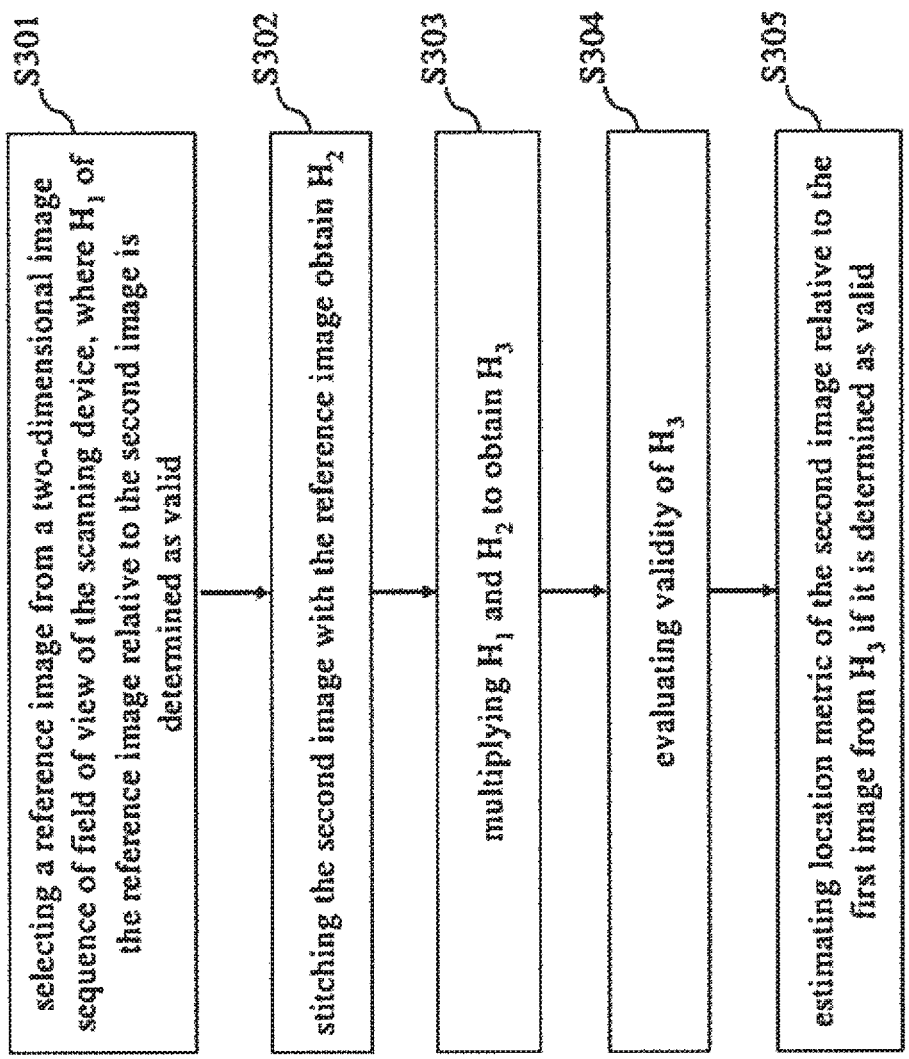
FIG. 3 illustrates a process for estimating location metric of one two-dimensional image of field of view of the scanning device relative to another.

FIG. 3 illustrates a process for estimating location metric of one two-dimensional image of field of view of the scanning device relative to another. As discussed above, the feedback to indicate if the second position is preferable for capturing a new 3D view is based on the estimated location metric of the second image relative to the first image. As illustrated in FIG. 3, to estimate said location metric, the processing unit 102 may be configured to first select a reference image from a two-dimensional image sequence of field of view of scanning device 101 at step 301, where the transformation matrix $H_1$ from that reference image to the first frame was determined to be valid. For instance, reference images can be taken at a specific time interval, such as every 500 ms.

At step 302, the second image is stitched onto the reference image to obtain a transformation matrix $H_2$.

At step 303, $H_2$ is then multiplied with $H_1$ to obtain a third transformation matrix $H_3$, which is assumed to represent the transformation between the first image and the second image.

Without loss of generalization, the reference image could be equal to the first image, in which case $H_1$ equals the identity matrix and doesn't need to be evaluated numerically. This is equivalent to the direct evaluation of the transformation between the first and second frame as described above.

There may exist situations where the computation of the transformation matrix between two images might not be possible. For instance, the number of features or the number of feature matches might not be enough to determine any transformation. In such case, the stitching fails, otherwise the stitching succeeds.

At step 304, in case the stitching succeeds, the obtained transformation matrix $H_3$ must be evaluated to check if it is valid and determine a measure of the spatial relationship between the first image and the second image. In one embodiment of the present invention where $H_1$, $H_2$ and $H_3$ is affine transformation matrix, the validity of transformation matrix $H_3$ may include decomposing $H_3$ to obtain at least one parameter describing spatial correspondence between pixels in the second image and the first image, that is to extract parameters such as $\theta$, $w$, $(s_x, s_y)$, $(t_x, t_y)$. The extracted parameters may be compared to predetermined thresholds so as to determine if $H_3$ is valid. For example, if the scale value of $(s_x, s_y)$ for x and y axes both lie in the range of [0.5, 2], then $H_3$ could be considered as acceptable. The same ideas applies to the other parameters.

In another embodiment of the present invention, evaluating the validity of transformation matrix $H_3$ may include: applying $H_3$ to the second image to obtain an intermediate image, that is to multiply $H_3$ with the pixel matrix of the second image and then calculating similarity between the intermediate image and the first image. A measure of similarity may be obtained by calculating normalized cross correlation (NCC) or normalized mutual information between the intermediate image and the first image, the former may lie in the range of [−1, 1] and the latter in the range of [0, 1]. The similarity could be compared with a predetermined threshold to determine if $H_3$ is valid.

At step 305, if $H_3$ is determined as valid, the location metric of the second image relative to the first image is estimated from this matrix. As mentioned above, the location metric for example could be a measure of overlap or rotation angle between the two images. Decomposition results of a valid $H_3$ between the second and first image could provide a solid estimation of location metric, such as the rotation angle. Decomposition of the transformation matrix into a 3×3 rotation matrix and a 3×1 translation vector may require the knowledge of intrinsic camera parameters, which can be obtained through camera calibration procedures in the field of computer vision. The rotation angle of a rotation $\theta$ matrix can be computed using the following relationship in a rotation matrix R: trace(R)=1+ 2cos($\theta$). The fraction of pixels in the intermediate image which contains information from the second image could provide the estimation of overlap between the two images.

In practice, the processing unit is configured to store several reference images during the movement of the scanning device, where the reference frame could be sampled at a certain interval. In order to limit the amount of data stored, the total number of reference images may be limited, therefore some references may be replaced by new ones after a while. The use of multiple reference images allows the tracking to continue/recover faster by switching to another reference image if tracking doesn't succeed any longer with the current frame. The tracking is said to have a limited history. When a reference image gets stored, the corresponding transformation matrix $H_1$ is also stored along with the reference image. This way $H_1$ never needs to be recomputed. The same selected reference frame might be reused for subsequent second image in the captured image sequence.

The transformation matrix between images is denoted with a single matrix, regardless of the mapping direction, but to be precise, if transformation matrix H corresponds to the mapping from second image pixel coordinate onto first image pixel coordinate, the opposite relationship from first image pixel coordinate to second image pixel coordinate is obtained using the inverse of the transformation matrix H.

Although embodiments of the invention are not limited in this regard, the terms "plurality" and "a plurality" as used herein may include, for example, "multiple" or "two or more". Exemplary embodiments according to the application can include various features described herein (individually or in combination). The terms "plurality" or "a plurality" may be used throughout the specification to describe two or more components, devices, elements, units, parameters, or the like.

It should be noted that the aforesaid embodiments are illustrative of this invention instead of restricting it, substitute embodiments may be designed by those skilled in the art without departing from the scope of the claims below. The wordings such as "include", "including", "comprise" and "comprising" do not exclude elements or steps which are present but not listed in the description and the claims. It also shall be noted that as used herein and in the appended claims, the singular forms "a", "an", and "the" include plural referents unless the context clearly dictates otherwise. In addition, while a particular feature of the invention can have been disclosed with respect to only one of several implementations/embodiments, such feature can be combined with one or more other features of the other implementations/embodiments as can be desired and advantageous for any given or particular function. This invention can be achieved by means of hardware including several different elements or by means of a suitably programmed computer. In the unit claims that list several means, several ones among these means can be specifically embodied in the same hardware item. The use of such words as first, second, third does not represent any order, which can be simply explained as names.

Support for Stitching of OCT Scans

Optical coherence tomography (OCT) scanning is a non-invasive depth-imaging technique that employs interferometric principles to obtain high resolution, cross-sectional tomographic images that characterize the depth structure of a sample. Particularly suitable for in vivo imaging of human tissue, OCT has shown its usefulness in a range of biomedical research and medical imaging applications, such as in ophthalmology, dermatology, oncology, and other fields, as well as in ear-nose-throat (ENT) and dental imaging.

OCT has been described as a type of "optical ultrasound", imaging reflected energy from within living tissue to obtain cross-sectional data. Both OCT and ultrasound scanning systems are considered to be depth-imaging apparatus, providing volume information to at least some depth below the surface for imaged anatomy. In an OCT imaging system, light from a wide-bandwidth source, such as a super luminescent diode (SLD) or other light source, is directed along two different optical paths: a reference arm of known length and a sample arm that illuminates the tissue or other subject under study. Reflected and back-scattered light from the reference and sample arms is then recombined in the OCT apparatus, modeled generally on interferometer principles. Interference effects are used to determine characteristics of the surface and near-surface underlying structure of the sample. Interference data can be acquired by rapidly scanning the sampling illumination across the sample. At each of several thousand points, OCT apparatus obtains an interference profile which can be used to reconstruct an A-scan with an axial depth into the material that is a factor of light source coherence. For most tissue imaging applications, OCT uses broadband illumination sources and can provide depth imaging content at depths of a few millimeters (mm) below a surface.

Initial OCT apparatus employed a time-domain (TD-OCT) architecture in which depth scanning is achieved by rapidly changing the length of the reference arm using some type of mechanical mechanism, such as a piezoelectric actuator, for example. TD-OCT methods use point-by-point scanning, requiring that the illumination probe be moved or scanned from one position to the next during the imaging session. More recent OCT apparatus use a Fourier-domain architecture (FD-OCT) that discriminates reflections from different depths according to the optical frequencies of the signals they generate. FD-OCT methods simplify or eliminate axial scan requirements by collecting information from multiple depths simultaneously and offer improved acquisition rate and signal-to-noise ratio (SNR). There are two basic implementations of Fourier-domain OCT: spectral domain OCT (SD-OCT) and swept-source OCT (SS-OCT).

SD-OCT imaging can be accomplished by illuminating the sample with a broadband source and dispersing the reflected and scattered light with a spectrometer onto an array detector, such as a CCD (charge-coupled device) detector, for example. SS-OCT imaging illuminates the sample with a rapid wavelength-tuned laser and collects light reflected during a wavelength sweep using only a single photodetector or balanced photodetector. With both SD-OCT and SS-OCT, a profile of scattered light reflected from different depths is obtained by operating on the recorded interference signals using Fourier transform analysis, such as using Fast-Fourier transforms (FFT), well known to those skilled in the signal analysis arts.

Because of their potential to achieve higher performance at lower cost, FD-OCT systems based on swept-frequency laser sources have attracted significant attention for medical applications that require subsurface depth imaging in highly scattering tissues. However, it can be unclear to the operator during scan acquisition whether or not image content from two nearby locations obtained using OCT scanning can be combined.

In the context of the present disclosure, the general term "scanner" relates to an optical system that projects a scanned light beam of broadband near-IR (BNIR) light that is directed to the tooth surface through a sample arm and acquired, as scattered light returned in the sample arm, for detecting interference with light from a reference arm used in OCT imaging of a surface. The term "raster scanner" relates to the combination of hardware components that scan light toward a sample, as described in more detail subsequently.

The term "subject" refers to the tooth or the gum or the jaw, or the implant or the preparation or other portion of a patient that is being imaged and, in optical terms, can be considered equivalent to the "object" of the corresponding imaging system.

In the context of the present disclosure, the phrase "broadband light emitter" refers to a light source that emits a continuous spectrum output over a range of wavelengths at any given point of time. Short-coherence or low-coherence, broadband light sources can include, for example, super luminescent diodes, short-pulse lasers, many types of white-light sources, and supercontinuum light sources. Most short coherence length sources of these types have a coherence length on the order of tens of microns or less.

According to an embodiment of the present disclosure, there can be provided a programmable light source that can provide variable wavelength illumination. The programmable light source can be used as a swept-source for scanned SS-OCT and other applications that benefit from a controllably changeable spectral pattern.

Figure 6A:
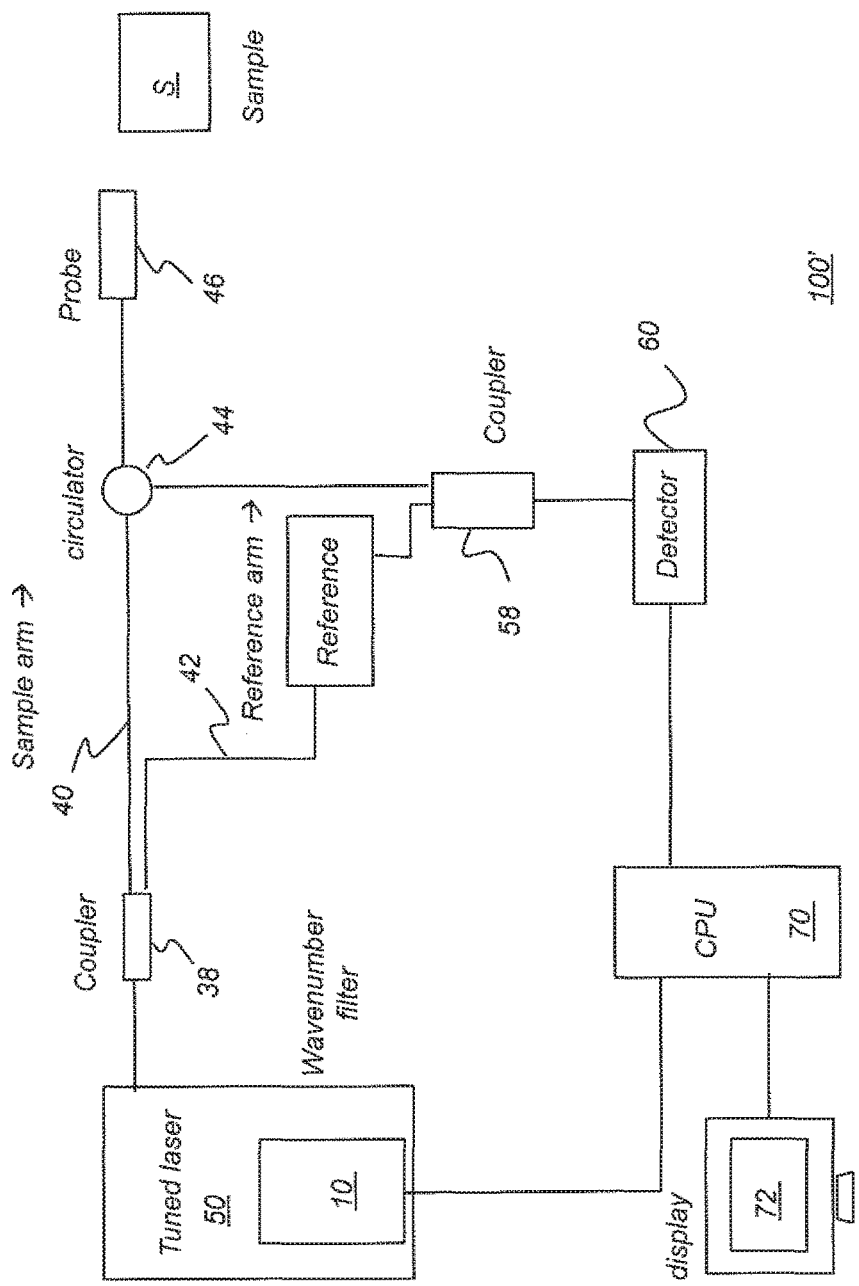
FIGS. 6A and 6B each show a swept-source OCT (SS-OCT) apparatus using a programmable filter according to an embodiment of the present disclosure.
Figure 6B:
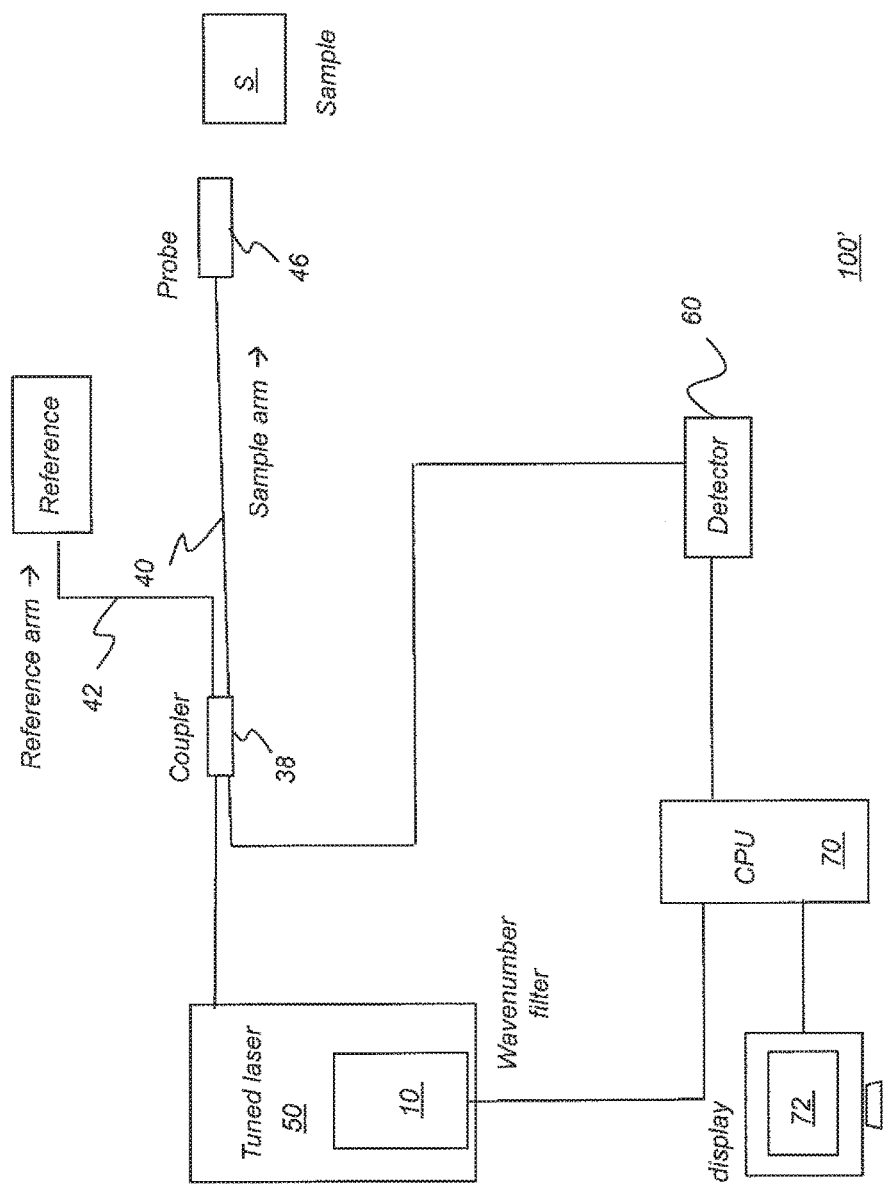

The simplified schematic diagrams of FIGS. 6A and 6B each show a swept-source OCT (SS-OCT) apparatus 100' using a programmable filter 10 according to an embodiment of the present disclosure. In each case, programmable filter 10 is used as part of a tuned laser 50. For intraoral OCT, for example, laser 50 can be tunable over a range of frequencies (wave-numbers k) corresponding to wavelengths between about 400 and 1600 nm. According to an embodiment of the present disclosure, a tunable range of 35 nm bandwidth centered about 830 nm is used for intraoral OCT.

In the FIG. 6A embodiment, a Mach-Zehnder interferometer system for OCT scanning is shown. FIG. 6B shows components for a Michelson interferometer system. For these embodiments, programmable filter 10 provides part of the laser cavity to generate tuned laser 50 output. The variable laser 50 output goes through a coupler 38 and to a sample arm 40 and a reference arm 42. In FIG. 6A, the sample arm 40 signal goes through a circulator 44 and to a probe 46 for measurement of a sample S. The sampled signal is directed back through circulator 44 (FIG. 6A) and to a detector 60 through a coupler 58. In FIG. 6B, the signal goes directly to sample arm 40 and reference arm 42; the sampled signal is directed back through coupler 38 and to detector 60. The detector 60 may use a pair of balanced photodetectors configured to cancel common mode noise. A control logic processor (control processing unit CPU) 70 is in signal communication with tuned laser 50 and its programmable filter 10 and with detector 60 and obtains and processes the output from detector 60. CPU 70 is also in signal communication with a display 72 for command entry and OCT results display. Probe 46 and display 72 also cooperate to provide a viewfinder that displays the field of view of the scanning device during scan operation. It is to be understood that CPU 70 may implemented in, for example, any suitable processing platform, computing platform, computing device, processing device, computing system, processing system, computer, processor, or the like, and may be implemented using any suitable combination of hardware and/or software, as may be suitable for specific applications or in accordance with specific design requirements.

Figure 7:
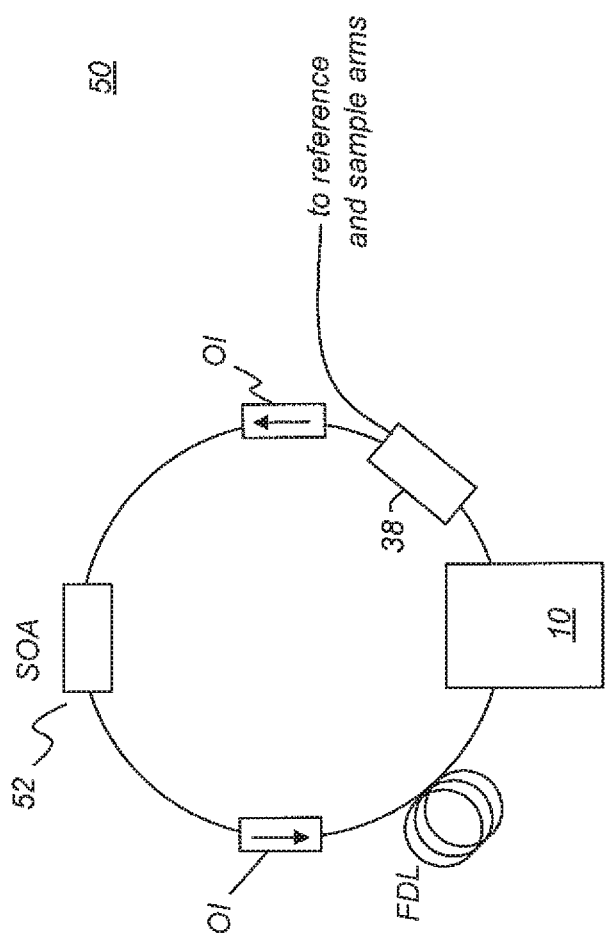
FIG. 7 is a schematic diagram that shows components of tuned laser according to an alternate embodiment of the present disclosure.

The schematic diagram of FIG. 7 shows components of tuned laser 50 according to an alternate embodiment of the present disclosure. Tuned laser 50 is configured as a fiber ring laser having a broadband gain medium such as a semiconductor optical amplifier (SOA) 52. Two optical isolators OI provide protection of the SOA from back-reflected light. A fiber delay line (FDL) determines the effective sweep rate of the laser. Filter 10 has an input fiber and output fiber, used to connect the fiber ring.

Figure 8:
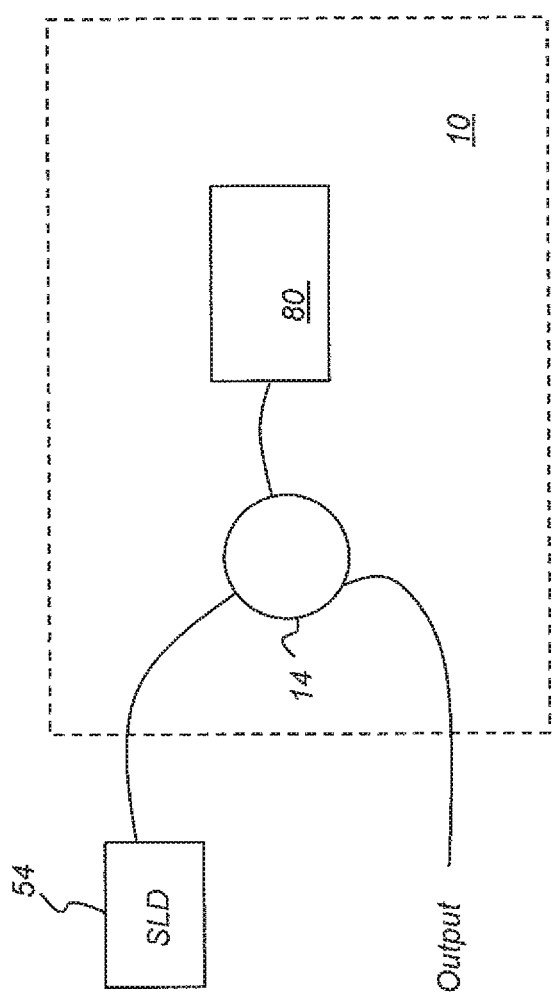
FIG. 8 is a schematic diagram that shows the use of a programmable filter for selecting a wavelength band from a broadband light source.

The schematic diagram of FIG. 8 shows the use of programmable filter 10 for selecting a wavelength band from a broadband light source 54, such as a super luminescent diode (SLD). Here, spatial light modulator 80 reflects a component of the broadband light through circulator 14. Circulator 14 is used to direct light to and from the programmable filter 10 along separate optical paths.

Figure 9:
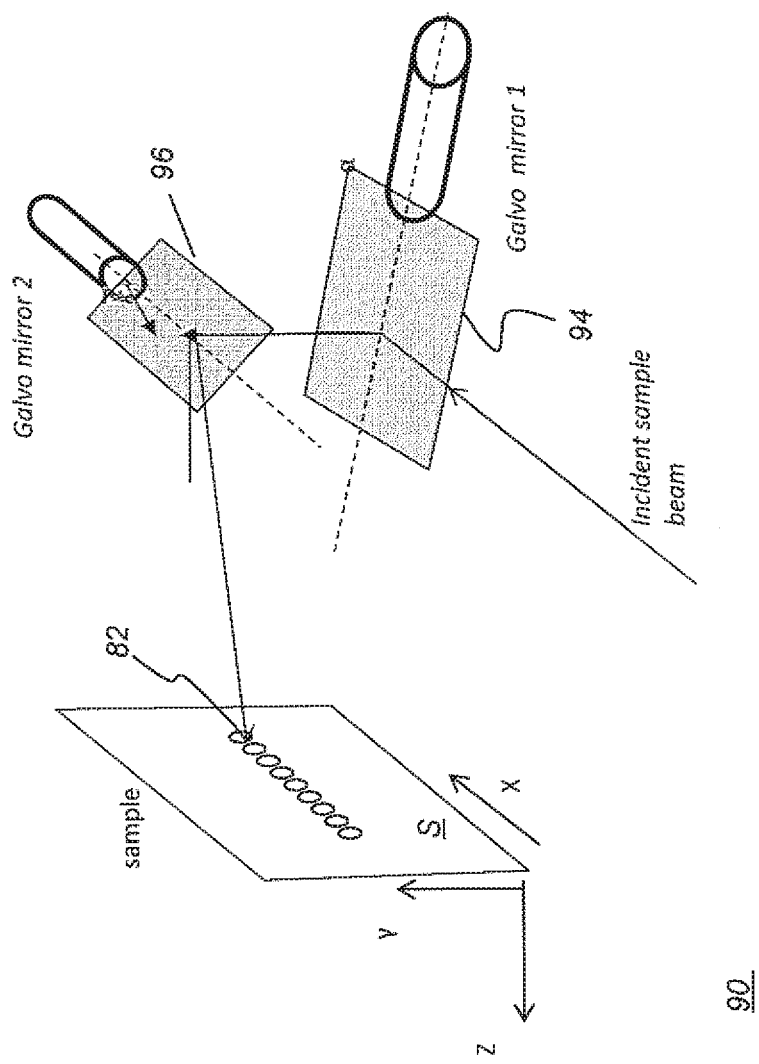
FIG. 9 is a schematic diagram showing galvo mirrors that cooperate to provide the raster scanning needed for OCT imaging.

As shown in the schematic diagram of FIG. 9, galvo mirrors 94 and 96 cooperate to provide the raster scanning needed for OCT imaging. In the arrangement that is shown, galvo mirror 1 (94) scans the wavelengths of light to each point 82 along the sample to generate data along a row, which provides the B-scan in the OCT scanning sequence, described in more detail subsequently. Galvo mirror 2 (96) progressively moves the row position to provide 2-D raster scanning to additional rows. At each point 82, the full spectrum of light provided using programmable filter 10, pixel by pixel of the spatial light modulator is rapidly generated in a single sweep and the resulting signal measured at detector 60 (FIGS. 6A, 6B).

Scanning Sequence for OCT Imaging

Figure 10A:
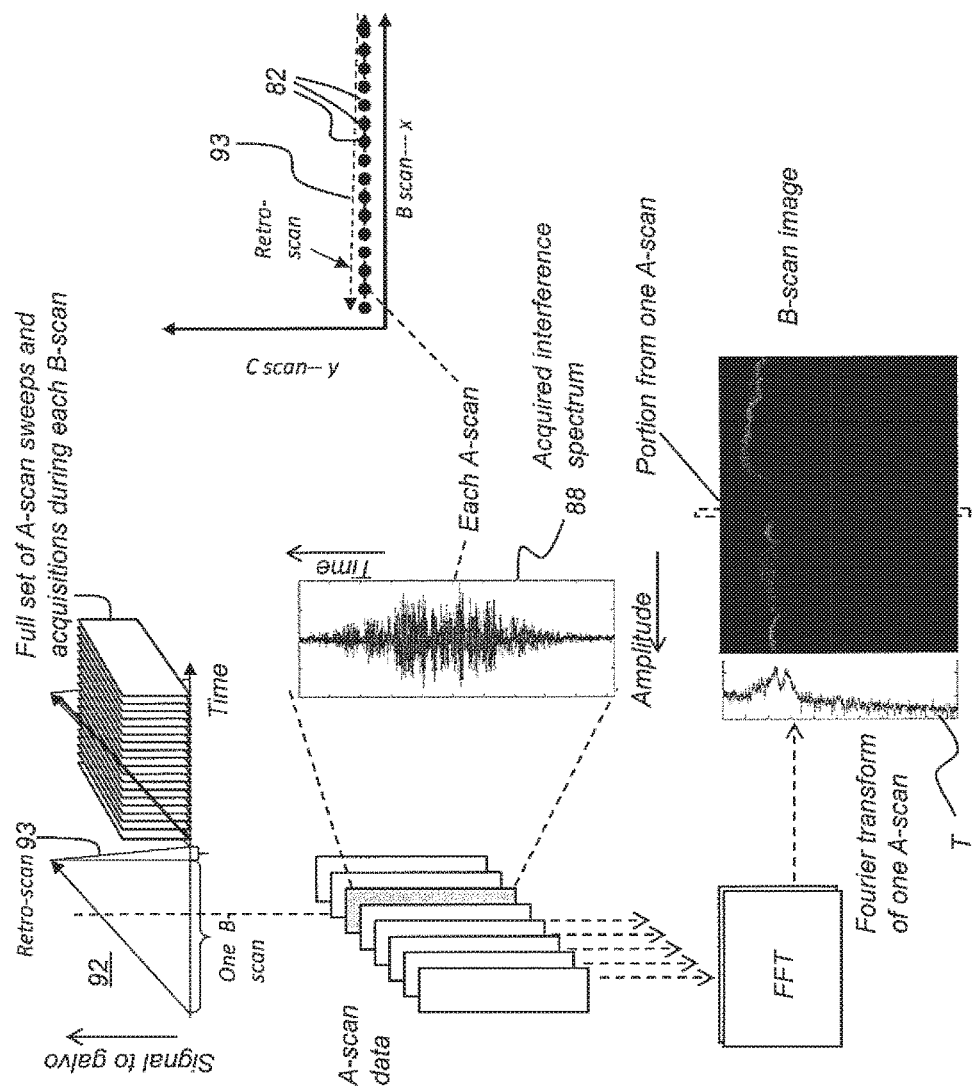
FIGS. 10A and 10B are schematic diagrams that show a scan sequence that can be used for forming tomographic images using the OCT apparatus of the present disclosure.
Figure 10B:
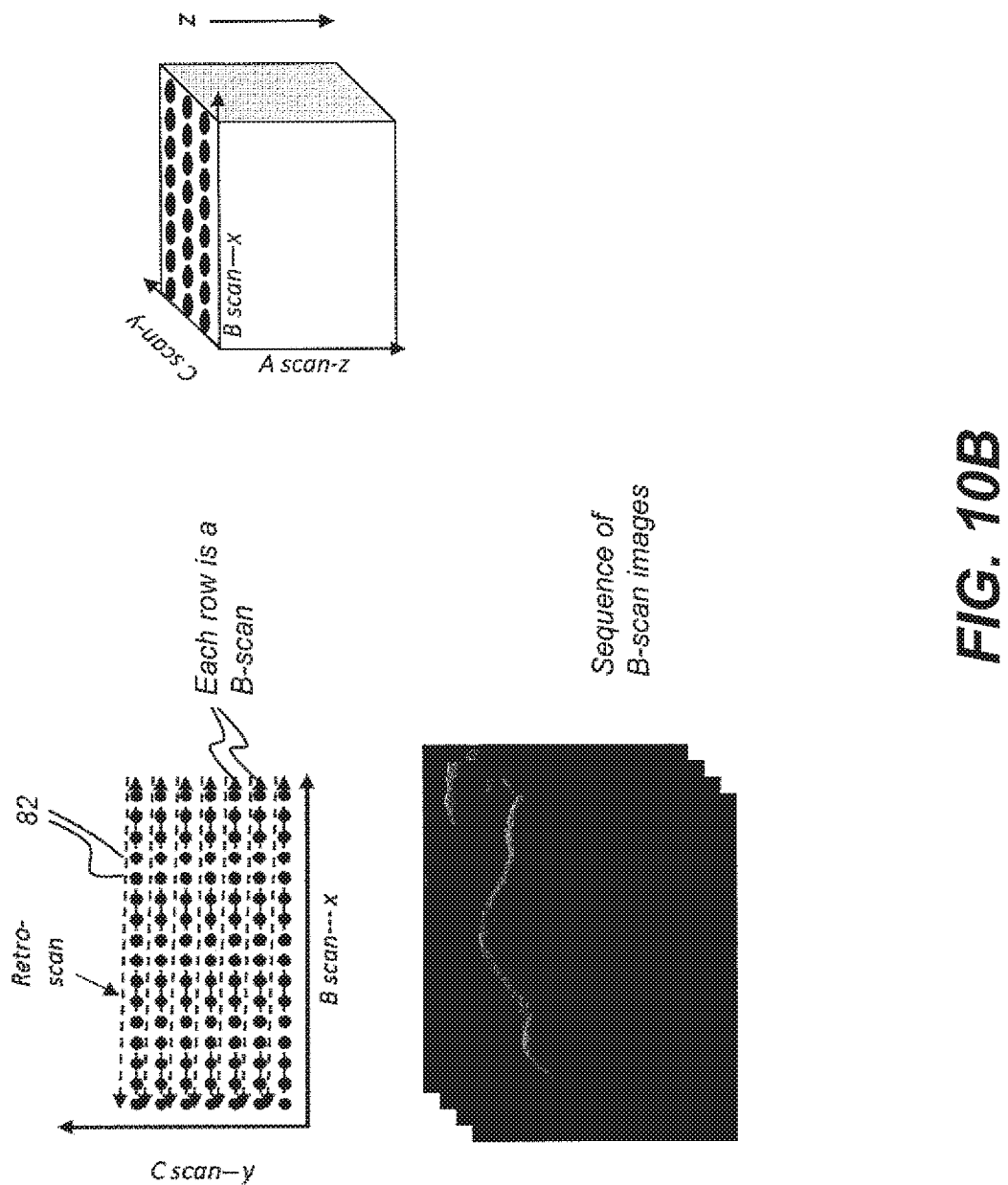

The schematic diagrams of FIGS. 10A and 10B show a scan sequence that can be used for acquiring scans and forming tomographic images using the OCT apparatus of the present disclosure. The sequence shown in FIG. 10A shows how a single B-scan image is generated and acquired. A raster scanner 90 (FIG. 9) scans the selected light sequence over sample S, point by point. A periodic drive signal 92 as shown in FIG. 10A is used to drive the raster scanner 90 galvo mirrors to control a lateral scan or B-scan that extends across each row of the sample, shown as discrete points 82 extending in the horizontal direction in FIGS. 10A and 10B. At each of a plurality of points 82 along a line or row of the B-scan, an A-scan or depth scan, acquiring data in the z-axis direction (FIG. 9), is generated using successive portions of the selected wavelength band. FIG. 10A shows drive signal 92 for generating a straightforward ascending sequence using raster scanner 90, with corresponding micro-mirror actuations, or other spatial light modulator pixel-by-pixel actuation, through the wavelength band. The retro-scan signal 93, part of drive signal 92, simply restores the scan mirror back to its starting position for the next line; no data is obtained during retro-scan signal 93.

It should be noted that the B-scan drive signal 92 drives the galvo mirror 94 for raster scanner 90 as shown in FIG. 9. At each incremental position, indicated as a point 82 along the row of the B-scan, an A-scan is obtained. To acquire the A-scan data, tuned laser 50 or other programmable light source sweeps through the spectral sequence that rapidly changes wavelengths as controlled by programmable filter 10. Thus, in an embodiment in which programmable filter 10 causes the light source to sweep through a 30 nm range of wavelengths, this sequence is carried out at each point 82 along the B-scan path. As FIG. 10A shows, the set of A-scan acquisitions executes at each point 82, that is, at each position of the scanning galvo mirror 94. By way of example, where a DLP micro-mirror device is used as spatial light modulator 80, there can be 2048 measurements for generating the A-scan at each position 82.

FIG. 10A schematically shows the information acquired during each A-scan. An interference signal 88, shown with DC signal content removed, is acquired over the time interval for each point 82, wherein the signal is a function of the time interval required for the sweep, with the signal that is acquired indicative of the spectral interference fringes generated by combining the light from reference and feedback arms of the interferometer (FIGS. 6A, 6B). The Fourier transform generates a transform T for each A-scan. One exemplary transform signal corresponding to an A-scan is shown by way of example in FIG. 10A.

From the above description, it can be appreciated that a significant amount of data is acquired over a single B-scan sequence. In order to process this data efficiently, a Fast-Fourier Transform (FFT) is used, transforming the time-based signal data to corresponding frequency-based data from which image content can more readily be generated.

In Fourier domain OCT, the A scan corresponds to one line of spectrum acquisition which generates a line of depth (z-axis) resolved OCT signal. The B scan data generates a 2-D OCT image along the corresponding scanned line.

Raster scanning is used to obtain multiple B-scan data by incrementing the raster scanner 90 acquisition in the C-scan direction. This is represented schematically in FIG. 10B, which shows how 3-D volume information, a 3D view, is generated using the A-, B-, and C-scan data.

In the context of the present disclosure, an OCT scan from a given position of the OCT scanner probe, forming the C-scan data as shown in FIG. 10B, for example, provides another type of "3D view" of an imaged object. This 3D view can then be used in analogous fashion to the 3D view generated from a handheld scanning device 101 as described previously with reference to FIG. 1.

As noted previously, the wavelength or frequency sweep sequence that is used at each A-scan point 82 can be modified from the ascending or descending wavelength sequence that is typically used. Arbitrary wavelength sequencing can alternately be used. In the case of arbitrary wavelength selection, which may be useful for some particular implementations of OCT, only a portion of the available wavelengths are provided as a result of each sweep. In arbitrary wavelength sequencing, each wavelength can be randomly selected, in arbitrary sequential order, to be used in the OCT system during a single sweep.

Figure 11:
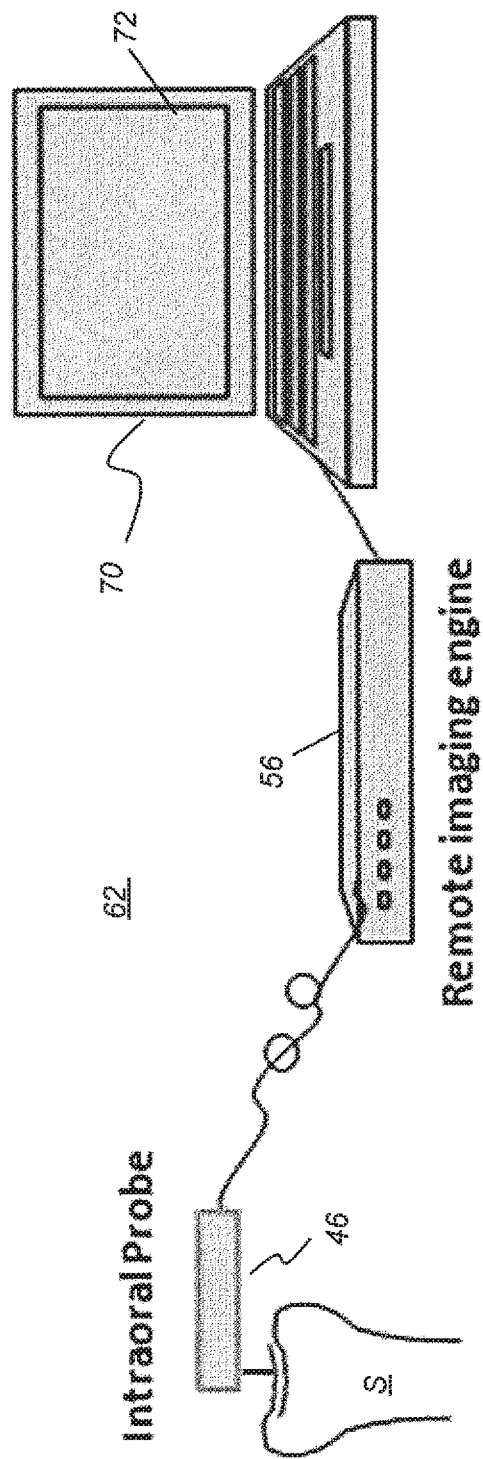
FIG. 11 is a schematic diagram that shows a probe and support components for forming an intraoral OCT imaging system.

The schematic diagram of FIG. 11 shows probe 46 and support components for forming an intraoral OCT imaging system 62. An imaging engine 56 includes the light source, fiber coupler, reference arm, and OCT detector components described with reference to FIGS. 6A-7. Probe 46, in one embodiment, includes the raster scanner 90 or sample arm, but may optionally also contain other elements not provided by imaging engine 56. CPU 70 includes control logic and display 72.

The preceding description gives detailed description of OCT imaging system 62 using a DLP micro-mirror array 30 as one useful type of spatial light modulator that can be used for selecting a wavelength band from programmable filter 10. However, it should be noted that other types of spatial light modulator 80 could be used to reflect light of a selected wavelength band. A reflective liquid crystal device could alternately be used in place of DLP micro-mirror array 30, for example. Other types of MEMS (micro-electromechanical system devices) micro-mirror array that are not DLP devices could alternately be used.

Processing for OCT Imaging

Figure 12:
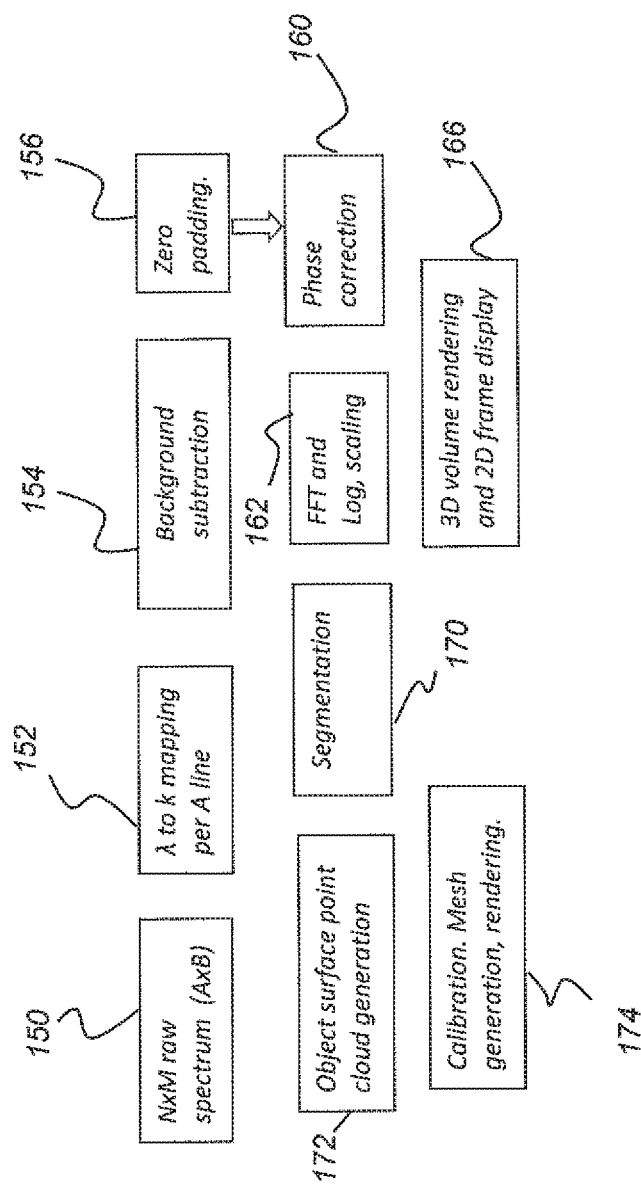
FIG. 12 is a logic flow diagram that shows a sequence for OCT processing to obtain OCT imaging content along with a surface point cloud extracted from the OCT content according to an embodiment of the present disclosure.

The logic flow diagram of FIG. 12 shows a sequence for OCT processing to obtain OCT imaging content along with a surface point cloud extracted from the OCT content according to an embodiment of the present disclosure. The raw 2-D spectral data 150 with numerous A scans per each B scan is provided over a linear wavelength λ, provided as M lines with N pixels per line. A mapping 152 then provides a wave-number value k for each corresponding wavelength λ. A background subtraction 154 executes, calculated along the B direction for each k value, and a line of background signal is obtained. Background subtraction 154, performed on each A line, helps to remove fixed pattern noise. In a zero padding operation 156 and a phase correction process 160 spectrum sampling is corrected and dispersion-induced OCT signal broadening obtained. An FFT processing step 162 provides processing and scaling of the phase-corrected data to provide input for a 3-D volume rendering and 2-D frame display rendering 166, useful for visualization and diagnostic support. At the conclusion of step 162, the OCT image content is available.

Subsequent processing in the FIG. 12 sequence then extracts the point cloud for surface characterization. A segmentation step 170 is then executed to extract the surface contour data from the OCT volume data. Object surface point cloud generation step 172 provides the surface point clouds of the measured object. Point clouds can then be calibrated and used for mesh rendering step 174 along with further processing. Geometric distortion calibration of OCT images can be executed in order to help correct shape distortion. Unless properly corrected, distortion can result from the scanning pattern or from the optical arrangement that is used by the OCT probe. Distortion processing can use spatial calibration data obtained by using a calibration target of a given geometry. Scanning of the target and obtaining the scanned data establishes a basis for adjusting the registration of scanned data to 3-D space, compensating for errors in scanning accuracy. The calibration target can be a 2-D target, imaged at one or more positions, or can be a 3-D target.

Segmentation step 170, object surface point cloud generation step 172, and mesh generation and rendering step 174 of the FIG. 12 sequence obtain surface contour data from OCT volume measurements. Importantly, results of these steps are the reconstructed surfaces of the object measured by OCT. This extracted OCT surface imaging content can be directly matched with results measured by a surface contour imaging device that shares the same coordinate system as the OCT content, using coordinate matching methods commonly known in the art, such as iterative closest point (ICP) matching. OCT and surface contour image data content can thus be automatically registered, either as point clouds or mesh, by ICP, without requiring additional steps.

The extracted OCT surface data, by itself or in registration with surface contour image data, can be displayed, stored, or transmitted to another computer or storage device.

Depending on applications and imaging conditions, various image segmentation algorithms can be used in segmentation step 170 to extract object surfaces. Image segmentation algorithms such as simple direct threshold, active contour level set, watershed, supervised and unsupervised image segmentation, neural network based image segmentation, spectral embedding and max-flow/min-cut graph based image segmentation, etc. are well known in the image processing fields and can be utilized; they can be applied to the entire 3-D volume or separately to each 2-D frame of the OCT data.

Figure 13B:
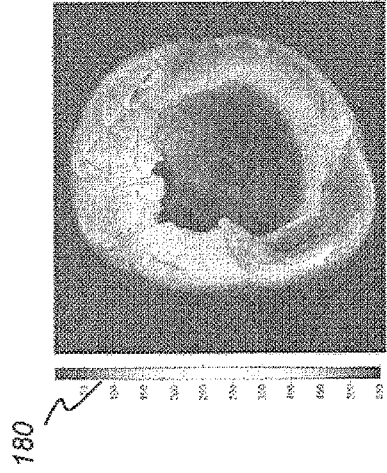
FIGS. 13A-13E show different types of imaging content acquired and generated as part of the OCT processing sequence, using the example of a tooth image having a severe cavity.
Figure 13A:
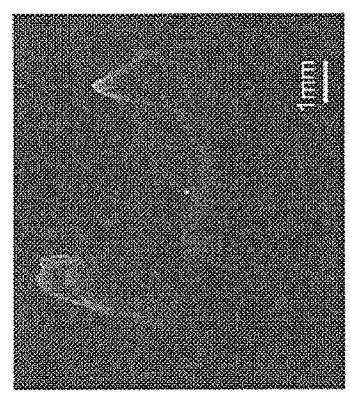
Figure 13E:
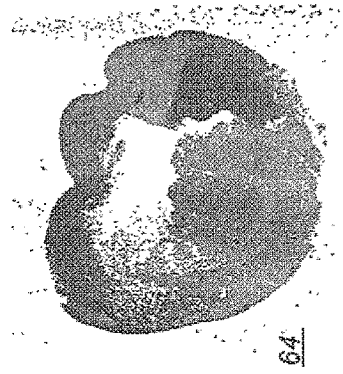
Figure 13D:
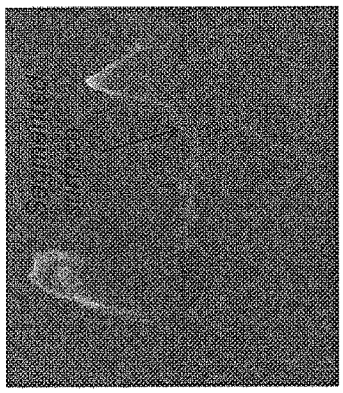
Figure 13C:
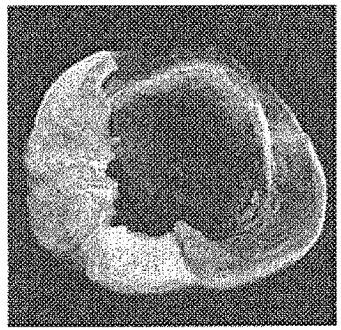

FIGS. 13A-13E show different types of imaging content acquired and generated as part of the OCT processing sequence, using the example of a tooth image exhibiting a severe cavity. FIG. 13A shows a 2-D slice that corresponds to a B-scan for OCT imaging. FIG. 13B shows a depth-encoded color projection of the tooth, with an optional color bar 180 as a reference. FIG. 13C shows a corresponding slice of the volume rendering obtained from the OCT imaging content. FIG. 13D shows the results of segmentation processing of FIG. 13A in which points along the tooth surface are extracted. FIG. 13E shows a surface point cloud 64 of the tooth generated from the OCT volume data. The surface point cloud 64 can be obtained from the OCT volume data following segmentation, as shown previously with respect to the sequence of FIG. 12.

3-D View Stitching for OCT Volume Content

A number of approaches can be used for stitching 3-D content obtained using a handheld intraoral scanning device that provides OCT imaging. According to an embodiment of the present disclosure, 3-D surface segmentation, as previously described with reference to the processing sequence in FIG. 12, can be used to facilitate stitching of the volume data from individual 3-D views. With respect to embodiments of the present disclosure, segmentation can be used to help determine whether or the positions used for an OCT imaging scan allows stitching to previously acquired 3-D OCT imaging results.

Figure 14:
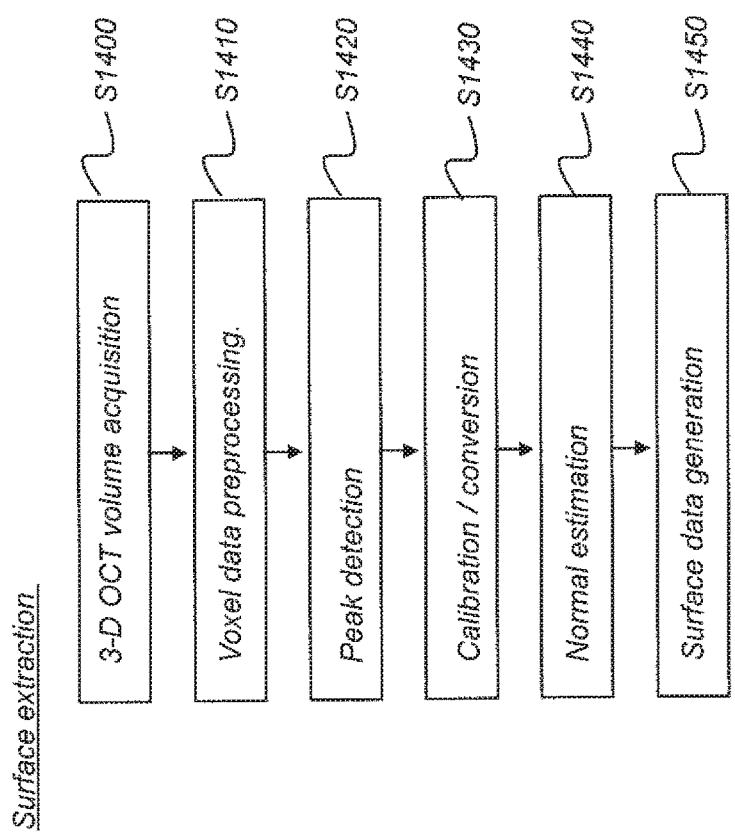
FIG. 14 is a logic flow diagram that shows a sequence for surface extraction of OCT data obtained using a handheld OCT scanning apparatus.

The logic flow diagram of FIG. 14 shows another example sequence for surface extraction of OCT data obtained using a handheld OCT scanning apparatus. In a volume acquisition step S1400, OCT scanning obtains a 3-D volume, as described with reference to preceding procedures and FIGS. 10A-13. A preprocessing step S1410 executes volume preprocessing. According to an embodiment of the present disclosure, preprocessing attempts to compensate for the high multiplicative noise that can result from OCT scanning and reconstruction. The logarithm of each voxel is obtained and an additive noise reduction algorithm is executed. This algorithm can use a Gaussian filter or median filter, for example, using filtering and noise reduction techniques familiar to those skilled in the imaging art.

The process of FIG. 14 then takes the exponent, in order to reverse effects of the logarithm filtering. An edge-preserving filter is generally preferred, in order to avoid shifts in the interface position effected by filtering. A peak detection step S1420 then executes in order to detect interfaces between distinct features, such as identifying significant gradients and edges, for example. Some types of peak detection algorithms include Sobel edge detection filtering, zero crossing of the second order derivative, and Gaussian fit on first order derivatives, for example. Along each B-scan line (FIGS. 10A-10B), the most pronounced response is identified. Additional processing in step S1420 can help to remove outlier data, such as data from random noise, for example.

Continuing with the processing shown in FIG. 14, a calibration step S1430 converts peak coordinates from voxel locations to 3-D world spatial units, such as using coordinates in millimeters. This process uses logic based on modeling of the fan scanning of the OCT imaging hardware, such as MEMS (micro-electromechanical systems) mirror scanning hardware, and uses evaluation of the range of the scanline. A surface normal estimation step S1440 selects a grouping of points surrounding a query point. This can use, for example, processing such as Principal Component Analysis (PCA) on a covariance matrix of the grouped points. PCA provides a 3×3 matrix which can be converted into 3 eigenvalues and 3 eigenvectors. This PCA processing is equivalent to the fitting of the grouped points by an ellipsoid, whose axes are given by the eigenvectors and the arm length is inversely proportional to the corresponding eigenvalue. The surface normal direction at the query point is defined as the eigenvector corresponding to the smallest eigenvalue. The direction of the calculated normal is then swapped to have a positive z-value.

A surface generation step S1450 can then generate a point cloud having surface normals; alternately, a surface mesh with corresponding normals can be generated. A point cloud with normals or a surface mesh with normals are typical data structures needed for 3D surface stitching.

According to an embodiment of the present disclosure, surface data available through OCT volume imaging can be used for techniques for providing real-time feedback to a user operating a three dimensional scanning device for three-dimensional imaging, e.g., the intraoral OCT imaging system 62. For example, the probe 46 may be manipulated by the user to capture three-dimensional volumes of an object from different positions, As described herein, in order to obtain a view for the global surface of an object, more than one 3D views shall be successively captured from different perspectives and the three-dimensional data for each view may be "stitched" all together at the same time or stitched to existing three-dimensional model using various stitching algorithms.

The CPU 70 may be configured to execute the steps as illustrated in FIG. 2, where a process for three-dimensional imaging according to one embodiment of the present invention is illustrated. Particularly, the CPU 70 can be configured to store (S201) a first two-dimensional image of field of view of probe 46 using a 3D surface contour (e.g., step 1450, FIG. 13E surface point cloud 64) at a first position where a first OCT three-dimensional volume of the object is captured; estimate (S202) location metric of a second two-dimensional image of field of view of probe 46 using a 3D surface contour at a second position relative to said first image while the probe 46 is being moved from said first position to said second position; and generate (S203) instructions on providing feedback to the user based on the location metric. According to an embodiment of the present disclosure, the location metric of the second two-dimensional image can be estimated (S202) using a field of view of probe 46 at the second position. In embodiments of the present invention, the feedback is provided to indicate whether the second position is adequate for capturing a second OCT three-dimensional volume for stitching process in three-dimensional imaging procedure.

Methods and/or arrangements of the present disclosure can be used to determine whether or not there is sufficient correlation between an obtained 3D view and a subsequent 3D view for the two views to be stitched in order to generate a larger, composite 3-D surface or volume that utilizes both views. The 3-D views can be 3-D surface data, in the form of a point cloud or mesh. Where volume data is obtained, stitching of 3-D views can be obtained by extracting the 3-D surface contour and using conventional 3-D surface stitching algorithms. Alternately, with volume data, stitching of the 3-D content can be directly performed. Further, an estimation (e.g., location metric) between the first 3D view and the second 3D view can be done either directly between these 3D views, or indirectly through the use of a reference 3D view according to methods and/or arrangements of the present disclosure.

System embodiments of the present disclosure (e.g., FIGS. 6A, 6B, or 11) can provide an output signal indicative of whether or not the 3-D surface data or the 3-D volume data can be stitched together. This output signal can generate displayed data on the system display or using a LED or other indication directly on the OCT probe itself. Similarly, for ultrasound or other volume-generating system, an indication can be provided using the display or probe indicator.

Figure 15:
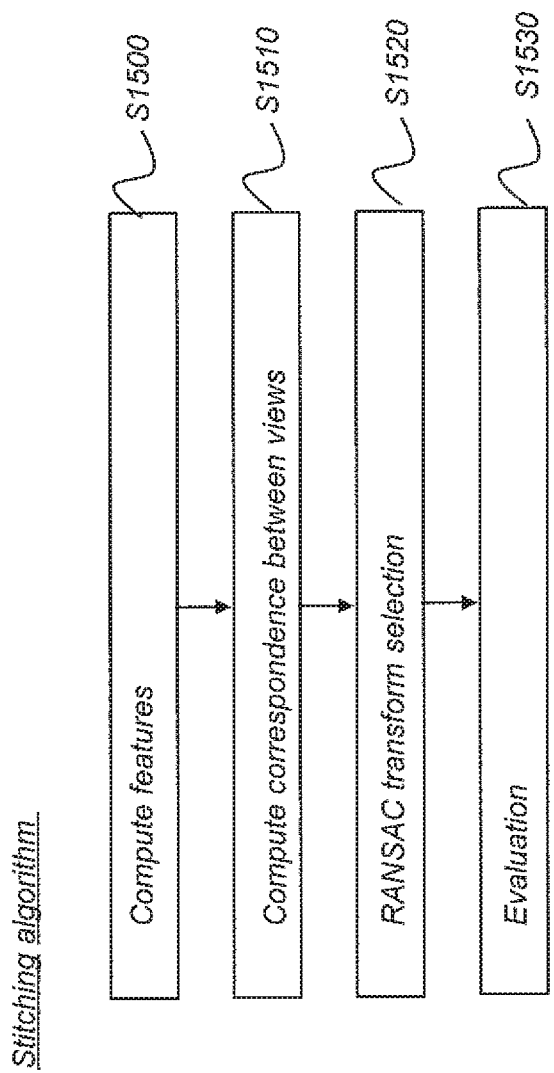
FIG. 15 is a logic flow diagram that shows a sequence for a 3-D stitching algorithm.

According to an embodiment of the present disclosure, the logic flow diagram of FIG. 15 can be used to execute a generic 3-D stitching algorithm, applicable to a 3-D surface or 3-D volume stitching workflow. In a compute features step S1500, features are defined by a position in 3-D and a feature vector. A feature distance is also defined. Feature definitions can be generated using 3-D SIFT (Scale Invariant Feature Transform) features for the 3-D volume. SIFT is used to identify and describe local features in images. Alternately, a Fast Point Feature Histogram for 3-D surface can be employed, using a point cloud with defined normals.

In a compute correspondences step S1510, processing computes correspondence between two views. For each feature f1 from view #1, a minimum distance to features in view #2 is calculated. A feature f2 can be identified and correlated to feature f1; otherwise, without commutative symmetry, correspondence can be discarded.

In a transform selection step S1520, a RANSAC transform selection executes. For example, three feature correspondences are selected to define a unique rigid transform between view #1 and view #2. Residual displacement for identified features can be computed using the RANSAC transform. Inliers can be counted, according to residual displacement below a predetermined threshold. The transform corresponding to the largest number of inliers can be retained.

In an evaluation step S1530, the selected transform from RANSAC can be used to determine whether or not adjacent images can be stitched together and to report results to the operator. Results can be reported on a display or by indicators provided on the OCT probe itself. The results of evaluation step S1530 can also serve to refine placement, such as using Iterative Closest Points (ICP) for 3-D surfaces. Alternately, maximum normalized cross-correlation for the 3-D volumes can be used for evaluation and stitching. A measure of the distance for the transform in the overlap between views can be detected and accepted if within a predefined range. Generally, this measure is obtained from the refinement algorithm, such as ICP or normalized cross-correlation. The results of evaluation step S1530 can be displayed or otherwise reported to the operator.

The processing can be used to determine whether or not there is sufficient correlation between an obtained view and a subsequent view for the two views to be stitched in order to generate a larger, composite 3-D surface or volume that utilizes both views. The 3-D views can be 3-D surface data, in the form of a point cloud or mesh. Where volume data is obtained, stitching of 3-D views can be obtained by extracting the 3-D surface contour and using conventional 3-D surface stitching algorithms. Alternately, with volume data, stitching of the 3-D content can be directly performed.

Method and/or system embodiments of the present disclosure can be used for 3-D volume imaging apparatus that perform depth imaging. Imaging apparatus for depth imaging can include OCT and other types of imaging that generate volume data, such as an ultrasound imaging apparatus. It can be appreciated that methods and/or systems of the present disclosure can be readily adapted for indicating whether or not overlapping 3-D views from such devices can be stitched together.

The invention claimed is:

1. A method for three-dimensional imaging, said method comprising:
   storing a first two-dimensional image of field of view from a handheld optical coherence tomography (OCT)

scanning device at a first position where a first three-dimensional OCT scan of an object is captured with the optical coherence tomography scanning device freely operated by a user;

estimating a location metric of a second two-dimensional image of field of view of the optical coherence tomography scanning device at a second position relative to said first image while said optical coherence tomography scanning device is being moved from said first position to said second position; and generating instructions on providing feedback to the user based on said location metric;

wherein said feedback is provided to indicate if said second position is adequate for capturing a second three-dimensional OCT scan, wherein providing feedback includes providing user perceivable light of a first color to indicate said second position is adequate and providing user perceivable light of a second color to indicate said second position is not adequate.

2. The method of claim 1 further comprising relating the first and second three-dimensional OCT scans using a surface stitching and/or volume stitching algorithm.

3. The method of claim 2 wherein stitching involves a feature-based matching.

4. The method of claim 1 further comprising displaying stitching results.

5. The method according to claim 1, wherein the object is the jaw, tooth or gum of a patient, an implant or a preparation.

6. The method of claim 1 further comprising:
generating first and second 3D surfaces by segmenting the OCT scan data acquired from scanning at first and second positions; and
stitching the first and second three-dimensional OCT scans using surface normal.

7. The method according to claim 1, wherein said location metric is estimated as one of the following: overlap between said first image and said second image; and rotation angle between said first image and said second image.

8. The method according to claim 7, wherein if said overlap is above 30% or if said rotation angle is less than 30 degrees, providing feedback to the user indicating that said second position is adequate for capturing said second three-dimensional scan.

9. The method according to claim 1, wherein providing feedback includes displaying representation of said first image superimposed on live video images of field of view of said OCT scanning device on a screen, and wherein
the location and appearance of said representation on the screen is configured to change with the motion of said OCT scanning device; and wherein
said representation is configured to present the first color to indicate said second position is adequate and the second color to indicate said second position is not adequate.

10. The method according to claim 9, wherein said representation of said first image is configured as a rectangle with a cross inside.

11. The method according to claim 1, wherein providing feedback includes projecting images onto the object, or emitting light of the first color to the object to indicate said second position is adequate and emitting light of the second color to indicate said second position is not adequate.

12. The method according to claim 1, wherein estimating the location metric of said second image relative to said first image includes:

a) selecting a reference image from a two-dimensional image sequence captured during its displacement from said first position to said second position,
where a transformation matrix $H_1$ of said reference image relative to the first image has been determined as valid;
b) stitching said second image with the reference image to obtain transformation matrix $H_2$;
c) multiplying $H_1$ and $H_2$ to obtain transformation matrix $H_3$;
d) evaluating the validity of transformation matrix $H_3$; and
e) estimating said location metric of said second image relative to said first image from transformation matrix $H_3$ if it is determined as valid.

13. The method according to claim 12, wherein transformation matrix $H_1$, $H_2$ and $H_3$ is an affine transformation matrix, and wherein evaluating the validity of said affine transformation matrix $H_3$ includes:
decomposing $H_3$ to obtain at least one parameter describing spatial correspondence between pixels in said second image and said first image; and
comparing the at least one parameter with predetermined thresholds to determine if said affine transformation matrix $H_3$ is valid, wherein
the at least one parameter is selected from the group of scale for both x and y axes, rotation angle, skew and translation for both x and y axes between said second image and said first image.

14. The method according to claim 12, wherein transformation matrix $H_1$, $H_2$ and $H_3$ is an affine transformation matrix, and wherein
stitching one image with another image to obtain the transformation matrix includes matching at least three pairs of feature points between the two images.

15. The method according to claim 12, wherein evaluating the validity of transformation matrix $H_3$ includes:
applying transformation matrix $H_3$ to said second image to obtain an intermediate image;
calculating similarity between said intermediate image and said first image; and
comparing the similarity with a predetermined threshold to determine if transformation matrix $H_3$ is valid.

16. A system for three-dimensional imaging, said system comprising:
an intraoral depth imaging scanner freely operated by a user to capture three-dimensional views of an object, wherein the depth imaging scanner is an optical coherence tomography scanner or an ultrasound scanner;
a processor configured to:
store a first two-dimensional image of field of view of said scanner at a first position where a first three-dimensional scan of the object is acquired;
estimate a location metric of a second two-dimensional image of field of view of said scanner at a second position relative to said first image while said scanner is being moved from said first position to said second position;
generate instructions on providing feedback to the user based on said location metric; and
an audible, tactile or visual user perceivable feedback unit configured to provide said feedback according to said instructions from said processor;
wherein said feedback is provided to indicate if said second position is adequate for capturing a second three-dimensional scan, where estimating the location metric of said second image relative to said first image includes:

a) selecting a reference image from a two-dimensional image sequence captured during scanner displacement from said first position to said second position, where transformation matrix $H_1$ of said reference image relative to the first image has been determined as valid;
b) stitching said second image with the reference image to obtain transformation matrix $H_2$;
c) multiplying $H_1$ and $H_2$ to obtain transformation matrix $H_3$;
d) evaluating the validity of transformation matrix $H_3$; and
e) estimating said location metric of said second image relative to said first image from transformation matrix $H_3$ if it is determined as valid.

17. The system according to claim 16, wherein said location metric is estimated as one of the following: overlap between said first image and said second image; and rotation angle between said first image and said second image, wherein if said overlap is above 30% or if said rotation angle is less than 30 degrees, providing feedback indicating that said second position is preferable for acquiring said second three-dimensional scan.

18. The system according to claim 16, wherein said feedback unit comprising a monitor for displaying live video images of field of view of said scanner;
said instructions on providing feedback including displaying representation of said first image superimposed on said live video images; and wherein
the location and appearance of said representation is configured to change with the motion of said scanner; and wherein
said representation is configured to present a first color to indicate said second position is adequate and a second color to indicate said second position is not adequate.

19. A method for three-dimensional imaging, said method comprising:
storing a first two-dimensional image of field of view of an intraoral depth imaging scanner at a first position where a first three-dimensional scan of an object is captured with said scanner freely operated by a user;
estimating location metric of a second two-dimensional image of field of view of the scanner at a second position relative to said first image while said scanner is being moved from said first position to said second position; and
generating instructions on providing feedback to the user based on said location metric; wherein
said feedback is provided to indicate if said second position is adequate for capturing a second three-dimensional scan, where said location metric is estimated using one of the following: overlap between said first image and said second image; and rotation angle between said first image and said second image, and where when said overlap is above 30% or when said rotation angle is less than 30 degrees, providing feedback indicating that said second position is adequate for capturing said second three-dimensional scan.

20. The method of claim 19, wherein the depth imaging scanner is an optical coherence tomography scanner or an ultrasound scanner.

21. An apparatus for three-dimensional imaging, comprising:
means for storing a first two-dimensional image of field of view of an OCT scanner at a first position where a first OCT scan of an object is captured with said handheld scanning device freely operated by a user;
means for estimating location metric of a second two-dimensional image of field of view of a scanning device at a second position relative to said first image while said OCT scanner is being moved from said first position to said second position; and
means for providing perceivable feedback to the user based on said location metric;
wherein said perceivable feedback is provided to indicate if said second position is adequate for capturing a second OCT scan, where said location metric is estimated at least as one of the following: overlap between said first image and said second image; and rotation angle between said first image and said second image, and wherein, when said overlap is above 30% or when said rotation angle is less than 30 degrees, providing feedback indicating that said second position is adequate for capturing said second OCT scan.

* * * * *